US00PP09903P

United States Patent [19]

Ackerman et al.

[11] Patent Number: Plant 9,903

[45] Date of Patent: May 27, 1997

[54] STRAWBERRY PLANT NAMED 'PS-592'

[75] Inventors: Stephen M. Ackerman, Salinas; Steven D. Nelson; Michael D. Nelson, both of Watsonville; Peter Salm, Capitola; Daniel T. Schmida, Watsonville, all of Calif.

[73] Assignees: Plant Sciences, Inc.; Berry Red, Inc., both of Watonsville, Calif.

[21] Appl. No.: 584,324

[22] Filed: Jan. 11, 1996

[51] Int. Cl.[6] ..... A01H 5/00

[52] U.S. Cl. ..... Plt./49

[58] Field of Search ..... Plt./48, 49

*Primary Examiner*—James R. Feyrer

*Attorney, Agent, or Firm*—Foley & Lardner

[57] ABSTRACT

This invention relates to a new and distinct winter planted short-day-type variety of strawberry known as 'PS-592'. This new variety is primarily adapted to the growing conditions of the central coast of California. It is particularly characterized by its strong vigorous plant with high yields, large berry size and its ability to remain in fruit production from April through November. The fruit is very attractive with excellent flavor and juiciness, moderate firmness and excellent holding quality.

3 Drawing Sheets

SUMMARY OF THE INVENTION

The present invention relates to a new and distinct short-day-type strawberry variety designated as 'PS-592'. This new variety is a result of a cross between proprietary and unpatented selections designated 'PS-61' and 'PS-143'. The variety is botanically known as *Fragaria×ananassa* Duch.

This new variety of strawberry resulted from a breeding program jointly sponsored by Plant Sciences, Inc. and Berry R&D, Inc., both of Watsonville, Calif., with the objective of developing new and distinct strawberry varieties. The seedling resulting from the aforementioned cross was asexually propagated by stolons in a nursery located in Lassen County, Calif., and was subsequently selected from a controlled breeding plot in Oxnard, Calif. in 1991. After its selection, the new variety was further asexually propagated in Lassen County, Calif. by stolons and extensively tested over the next several years in fruiting fields near Watsonville, Calif. This propagation and reproduction has demonstrated that the combination of traits disclosed herein as characterizing the new variety are fixed and remain true-to-type through successive generations of asexual reproduction.

BRIEF DESCRIPTION OF THE FIGURES

The accompanying color photographs show typical specimens of the new variety at various stages of development as nearly true as it is possible to make in color reproductions.

DESCRIPTION OF THE NEW VARIETY

Figure 1:
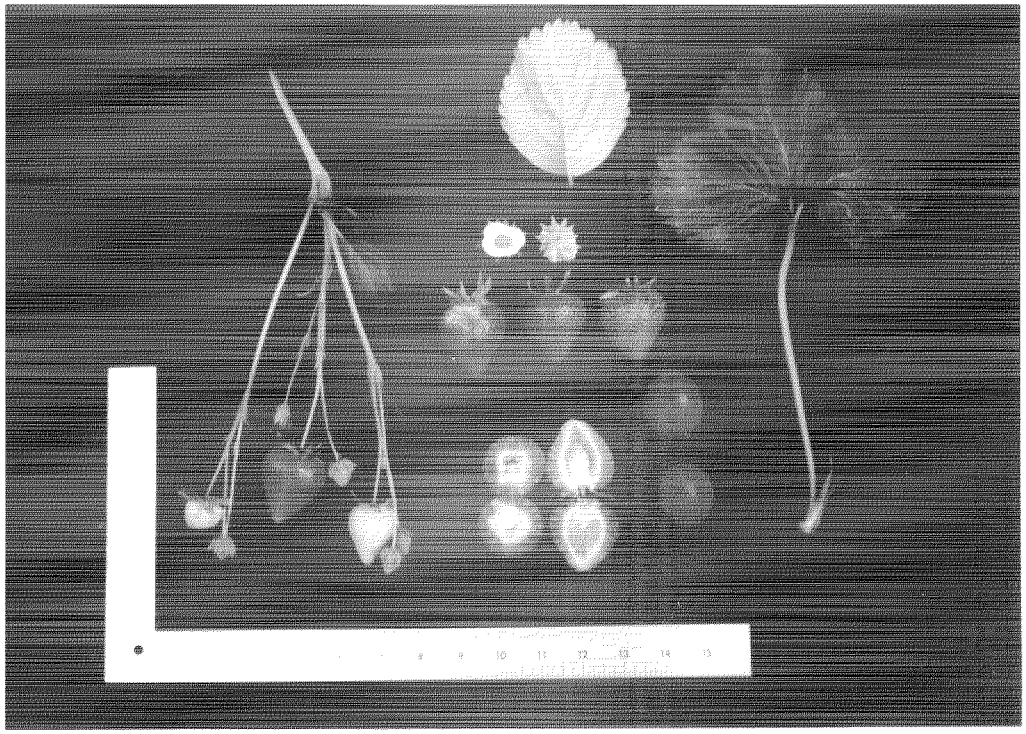
FIG. 1 shows typical plant parts of the new variety including leaves (both the lower surface of a mature terminal leaflet, and the upper surface of a mature trifoliate leaf). Cross-sectional and longitudinal views of mature fruit illustrate typical light flesh and conspicuous core and core cavity. Also shown is an inflorescence with the primary berry being mature and harvestable demonstrating typical fruit distribution, shape and size.
Figure 2:
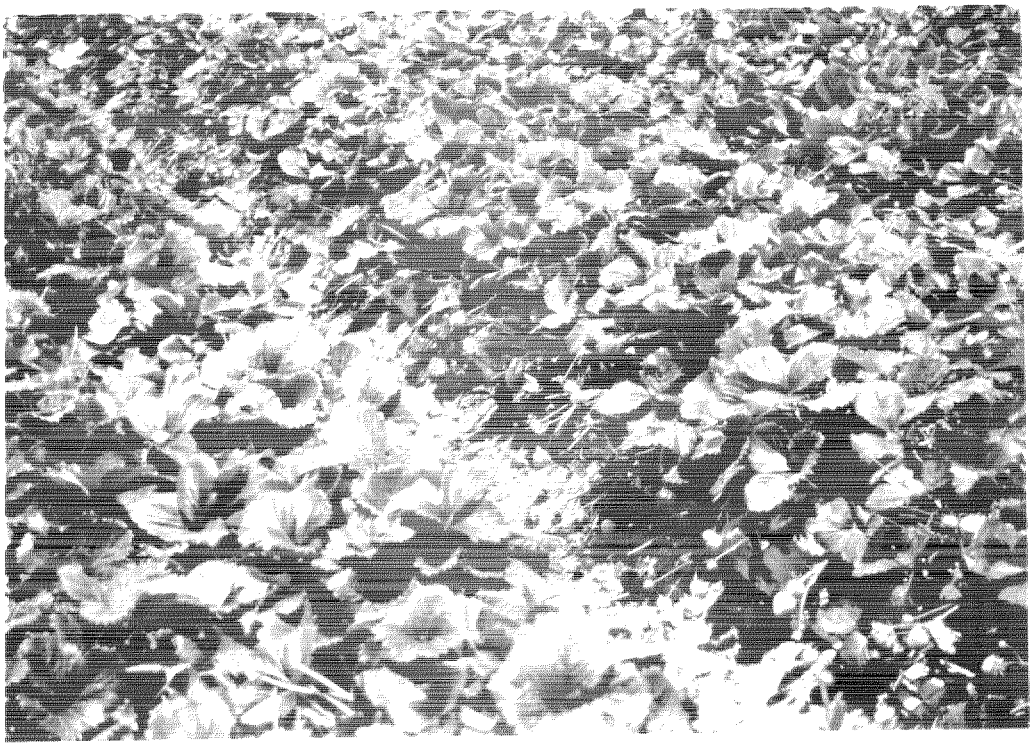
FIG. 2 shows typical plant growth, flowering and fruiting characteristics in early July 1995. The photograph illustrates the plant vigor, long inflorescences, and upright growth habit.
Figure 3:
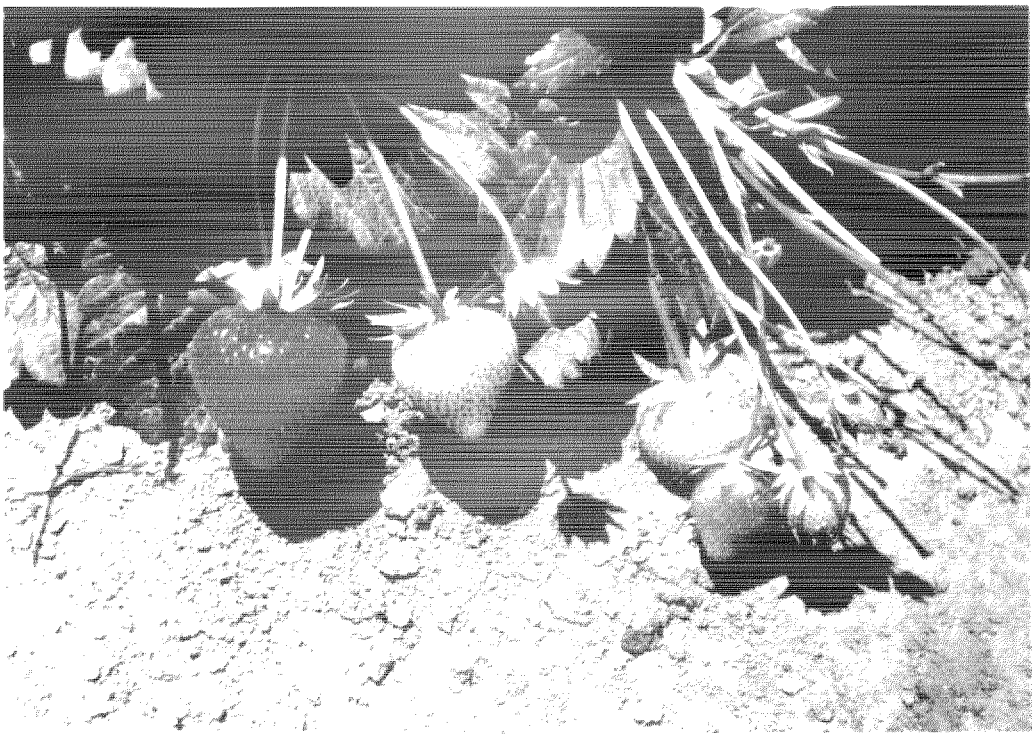
FIG. 3 shows a close-up of typical plant growth, flowering and fruiting characteristics in early July 1995.
Figure 4:
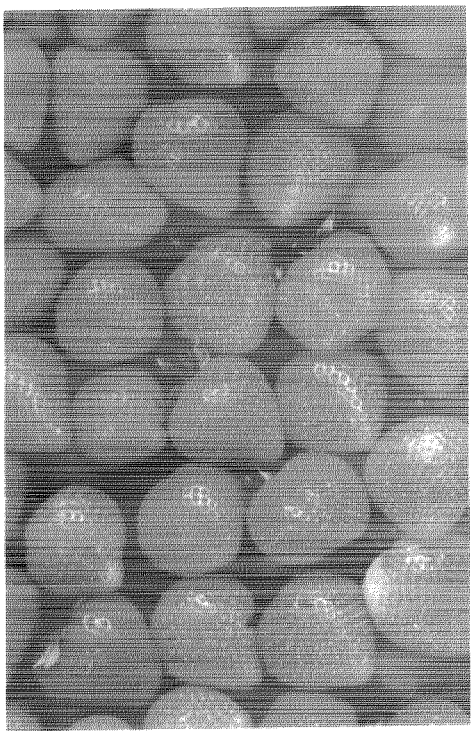
FIG. 4 shows a close-up view of fruit harvested in early July 1995 and packed in a standard twelve-dry-pint-crate.
Figure 4:
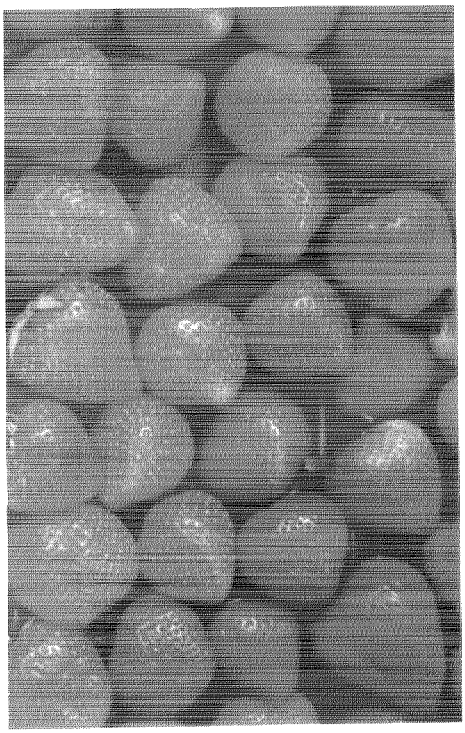

'PS-592' is primarily adapted to the climate and growing conditions of the central coast of California. This region provides the necessary winter temperatures required for it to produce a strong vigorous plant and to remain in fruit production from April through November. The nearby Pacific ocean provides the needed humidity and cool temperatures to maintain fruit quality during the summer production months.

'PS-592' is a large vigorous plant. When provided with optimum chilling in nursery propagation fields prior to being dug, and artificial cold storage prior to being planted, the plant of the new variety is larger and more vigorous than the variety claimed in U.S. Pat. No. P.P. 8,205 and now designated 'PS-118' and the variety 'Selva' (U.S. Pat. No. P.P. 5,266). 'PS-592' produces fewer runners per plant in the fruiting fields than both 'PS-118' and 'Selva'. The plant of 'PS-592' is also more open and less compact than 'PS-118' and more upright in growth habit than 'Selva'. The foliage of the new variety is noticeably lighter in color than 'PS-118' yet similar to 'Selva'. 'PS-592' leaves are larger and less rounded than 'PS-118' with fewer but deeper serrations than both 'PS-118' and 'Selva'. Petioles are longer in length and larger in diameter than both 'PS-118' and 'Selva'. Table 5 summarizes foliage characteristics of 'PS-592', 'PS-118' and 'Selva'. 'PS-592' is capable of long season fruit production with fruit of excellent size and good quality during the entire season when provided with optimum chilling in nursery propagation fields, and artificial cold storage, prior to being planted. Fruit production begins as early as late March to early April and may continue into November if rains and cold temperatures do not prevent the harvest. Accordingly, 'PS-592' fruit production commences earlier, with a heavier April crop than 'PS-118' but is similar to 'Selva' with respect to this characteristic. 'PS-592' season average fruit size is larger than both 'PS-118' and 'Selva' with total yields exceeding both 'PS-118' and 'Selva' (Table 1).

The fruit of 'PS-592' is smoother with fewer longitudinal creases and better overall appearance and gloss than 'Selva'. Table 3 summarizes fruit quality performance ratings. 'PS- 592' does not tend to produce seedy tips at the apex of the fruit. Both 'PS-118' and 'Selva' produce seedy tipped fruit during certain times of the year. The seeds of 'PS-592' do not protrude from the surface of the fruit. In contrast, 'PS-118' tends to have seeds that protrude from the surface. The fruit color of 'PS-592' is noticeably lighter than 'PS-118' but slightly darker than 'Selva'. 'PS-592' has a lighter internal flesh color than either 'PS-118' or 'Selva'. The fruit of 'PS-592' is more conical in shape (less rounded) than 'PS-118', typically with a more acute apex than either 'PS-118' and 'Selva'.

Flavor panels have rated 'PS-592' as having better flavor than either 'PS-118' or 'Selva' (Table 4). The total inflorescence length of 'PS-592' is longer than either 'PS-118' or 'Selva'. The average primary peduncle length during June is shorter and thicker than 'PS-118' and slightly longer and thicker than 'Selva'. The primary pedicel is similar in length to 'Selva' but longer than 'PS-118' and larger in diameter than both. The inflorescence characteristics are outlined in Table 6.

SPECIFIC DESCRIPTION OF THE NEW VARIETY

The following is a detailed description of 'PS-592', including the variety's morphological, electrophoretic, pest and disease reaction characteristics. This detailed description is based on observations taken during May and June of 1995 in Salinas, Calif. Some characteristics were rated at different times and therefore the date of the evaluation is listed. These measurements and ratings were made from plants dug from a high-elevation nursery located in Lassen County, Calif. in October 1994 and planted in Salinas, Calif. in November 1995. The phenotypic characteristics of the new variety may vary slightly, depending upon variations in environmental factors, including weather (temperature, humidity and light intensity), day length, soil type and location, without any change in genotype of the plant. 'PS-592' has not been observed under all possible environmental conditions. Color terminology follows the Munsell Book of Colors, Munsell Color, Baltimore, Md. (1976).

FRUIT CHARACTERISTICS

'PS-592' fruit, fruit production and runner production (fruiting field) characteristics are compared to those of 'PS-118' and 'Selva' in Table 1.

TABLE 1

1994 market fruit yield, fruit size and runner production characteristics from plants harvested from April through November 1994 of 'PS-592' from a high elevation nursery (McArthur, California) compared with standard cultivars dug October 20, 1993 and planted November 9, 1993 in Salinas, California

| CULTIVAR | APRIL YIELD GM/PL | TOTAL YIELD GM/PL | AVERAGE FRUIT SIZE G/FR | AVERAGE RUNNERS/ PL |
|---|---|---|---|---|
| 'PS-592' | 108 | 2015 | 26.7 | 0.05 |
| 'PS-118' | 43 | 1351 | 21.7 | 0.12 |
| 'SELVA' | 90 | 1414 | 22.8 | 0.20 |

TABLE 2

Comparison of primary fruit characteristics of 'PS-592', 'PS-118' and 'Selva' from Salinas, California, May 31, 1995

| CHARACTER | 'PS-592' | 'PS-118' | 'SELVA' |
|---|---|---|---|
| Munsell Color | 7.5R 3/12 to 7.5R 4/12 | 7.5R 3/10 to 7.5R 3/8* | 7R 4/11* |
| Fruit Length mean (cm) | 5.8 | 4.7 | 5.2 |
| Fruit Width mean (cm)** | 6.1 | 5.2 | 5.1 |
| Calyx Diameter mean (cm) | 6.8 | 6.0 | 5.1 |
| Sepals/Berry mean | 16.3 | 15.5 | 15.6 |

*'PS-118' and 'Selva' fruit color according to Nelson et al, U.S. Plant Pat. No. 8,205.
**Width was measured across the widest part of the berry, typically across the shoulders.

TABLE 3

Comparison of 1994 fruit quality characteristics of 'PS-592', 'PS-118' and 'Selva'*

| CHARACTER | 'PS-592' | 'PS-118' | 'SELVA' |
|---|---|---|---|
| Skin Firmness | 7.3 | 8.3 | 7.6 |
| Fruit Appearance | 7.7 | 7.7 | 6.8 |
| Fruit Gloss | 8.0 | 8.2 | 6.6 |

*Results are from replicated holding tests performed from April through October 1994 in Salinas, California. Ratings are based on a scale from 1–10; the higher the rating, the stronger the skin and the more attractive and glossy the berry.

TABLE 4

Comparison of 1995 flavor test summary of 'PS-592', 'PS-118' and 'Selva'.*

| CHARACTER | 'PS-592' | 'PS-118' | 'SELVA' |
|---|---|---|---|
| Rating | 3.6 | 3.5 | 2.4 |

*Results are an average of 3–4 flavor tests from fruit harvested from Salinas, California after being held for 2–3 days in cold storage. Ratings are based on scores of 1–5, 5 being the best.

The fruit is large in size, characteristically conical in shape and very attractive. Primary berries are very large, typically wider at the shoulders than long with some longitudinal creases and irregular shapes. The secondary and tertiary berries are typically longer than wide and mostly symmetrically conic in shape. The fruit surface is medium red in color with a very light colored flesh and white core. Fruit characteristics of 'PS-592', 'PS-118' and 'Selva' are compared in Table 2.

The fruit surface is smooth and the seeds do not protrude from the surface of the fruit. The seeds are yellow and only darken slightly with prolonged exposure to direct sunlight. The seeds are spaced evenly over the surface of the berry with seedy tipped fruit rare. The flesh is moderately firm, very glossy and juicy, with good texture and flavor. Fruit quality and flavor characteristics of 'PS-592' are shown in Tables 3 and 4.

The calyx of the primary berry is large in diameter with overlapping sepals. The calyx may attach slightly below the base of the fruit and may be slightly reflexed, occasionally developing a slight neck. The sepals are elliptical to ovate in shape with acute apexes and very few serrations. Fruit skin is considered only slightly susceptible to cracking due to rain. Pollination is rarely adversely affected by rain.

PLANT CHARACTERISTICS

The plant of 'PS-592' is large in size with multiple crowns producing very few runners if given the proper chilling levels prior to being dug, and artificially, prior to being planted. Excessive chilling will result in an over-vigorous, dense plant with a reduction in total fruit yield and increased runner production. The foliage grows upright on long thick petioles. The plant canopy remains relatively open if exposed to the proper chilling and cold storage, but may become dense if over-chilled and/or over-stored. The plant canopy has a relatively medium-light colored appearance.

FOLIAGE CHARACTERISTICS

'PS-592' foliage characteristics are compared to those of 'PS-118' and 'Selva' in Table 5.

TABLE 5

Comparison of leaf characteristics of 'PS-592', 'PS-118' and 'Selva' from Salinas, California, May 19, 1995.

| CHARACTER | 'PS-592' | 'PS-118' | 'SELVA' |
|---|---|---|---|
| Munsell Leaf Color (upper surface) | 7.5GY 4/4 | 7.5GY 3/4* | 7.5GY 4/4* |
| Terminal Leaflet length mean (cm) | 9.8 | 8.4 | 9.8 |
| Terminal Leaflet width mean (cm) | 8.2 | 7.7 | 8.3 |
| Terminal Leaflet ratio (L/W) | 1.21 | 1.09 | 1.19 |
| Petiole Length mean (cm) | 21.4 | 20.1 | 19.8 |
| Petiole Width mean (mm) | 5.4 | 4.7 | 5.2 |
| Petiolule Length mean (mm) | 10.8 | 10.0 | 10.8 |
| Serrations/Leaf | 20.1 | 20.7 | 24.9 |
| Serration Depth mean (mm) | 6.7 | 5.8 | 5.2 |

*'PS-118' and 'Selva' leaf color according to Nelson et al., U.S. Plant Pat. No. 8,205.

As shown in Table 5, the foliage of 'PS-592' is relatively large in size, glossy, medium-light in color and moderately rugose. The terminal leaflet is much longer than wide as described by the length/width ratio. Leaflets have relatively large and deep serrations at the margins, with moderately acute apexes. These serrations typically occur singly and very seldom in doubles. Petioles are considered long and thick in diameter with bract leaflets commonly occurring singly or in pairs. Pubescence on the petioles grows irregularly perpendicular to the petiole and irregularly parallel to the upper and lower leaf surface.

FLOWERS AND INFLORESCENCES

'PS-592' inflorescence characteristics are compared to those of 'PS-118' and 'Selva' in Table 6.

TABLE 6

Comparison of inflorescence characteristics of 'PS-592', 'PS-118' and 'Selva' from Salinas, California, June 6, 1995

| CHARACTER | 'PS-592' | 'PS-118' | 'SELVA' |
|---|---|---|---|
| Inflorescence Length mean (cm) | 38.2 | 29.3 | 31.9 |
| Primary Peduncle Length mean (cm) | 11.5 | 14.2 | 9.7 |
| Primary Peduncle Width mean (mm) | 6.6 | 4.6 | 5.2 |
| Primary Pedicel Length mean (cm) | 11.7 | 7.0 | 11.3 |
| Primary Pedicel Width mean (mm) | 4.0 | 2.8 | 3.1 |

The inflorescences of 'PS-592' are long, extending the flowers and fruit beyond the foliage during much of the season. The ripening fruit maybe observed hanging down alongside the plant bed and into the furrows during the summer months. The primary peduncle is typically short and thick during April and May, but lengthens as the fruiting season progresses. The pedicel holding the primary berry is considered long and thick and may originate singly from the apex of the primary peduncle or from one of the secondry peduncles. Secondary and tertiary berries are borne on pedicels arising from secondary peduncle apices. The inflorescence characteristics of 'PS-592', 'PS-118' and 'Selva' are shown in Table 6.

'PS-592' flowers are large and occasionally seen above the canopy of the plant. Anthers produce an abundance of pollen for good pollination, even during adverse weather conditions when pollination of other varieties may be compromised. Flowers produce an average of 6 to 8 obovate shaped petals per flower. Typically a bract leaf is borne on a long petiole which originates at the primary peduncle apex alongside the base of one of the secondary peduncles. Bract leaves may also occur at the apex of secondary peduncles. Pubescence occurs on all peduncles and pedicels, growing irregularly parallel to the primary pedicel and more irregularly perpendicular to the primary peduncle.

ISOZYMES IN LEAF EXTRACT

'PS-592'0 isozyme banding characteristics are compared to those of 'PS-118' and 'Selva' in Table 7.

TABLE 7

'PS-592' Isozyme banding patters compared to 'PS-118' and 'Selva'.

| CULTIVAR | PGI | PGM |
|---|---|---|
| 'PS-592' | A8 | C2 |
| 'PS-118' | A7 | C4 |
| 'Selva' | A2 | C2 |

Studies of protein polymorphism in strawberry by the starch gel electrophoresis method were conducted Plant Sciences, Inc. characterize this newly developed variety and distinguish it from similar appearing varieties.

Isozymes were extracted from young leaves and characterized, using starch gel electrophoresis techniques. The following isozymes were characterized: phosphoglucoisomerase (PGI: EC 5.3.1.9) and phosphoglucomutase (PGM: EC 2.7.5.1).

The testing used both field and greenhouse grown plant material, all grown in Watsonville, Calif. Newly mature leaves (0.5 g fresh weight) from the growing crowns were used. Samples were collected in the morning, held at 4° C. and analyzed within six hours.

The tissue preparation, extraction and staining methods utilized are as reported in Arulsekar et al., *HortScience* 21(4): 928–933. Following electrophoresis, the gel was sliced and stained for each enzyme system. Banding patterns were interpreted as they developed, and gel slices were fixed in 50% glycerol.

Figure 5:
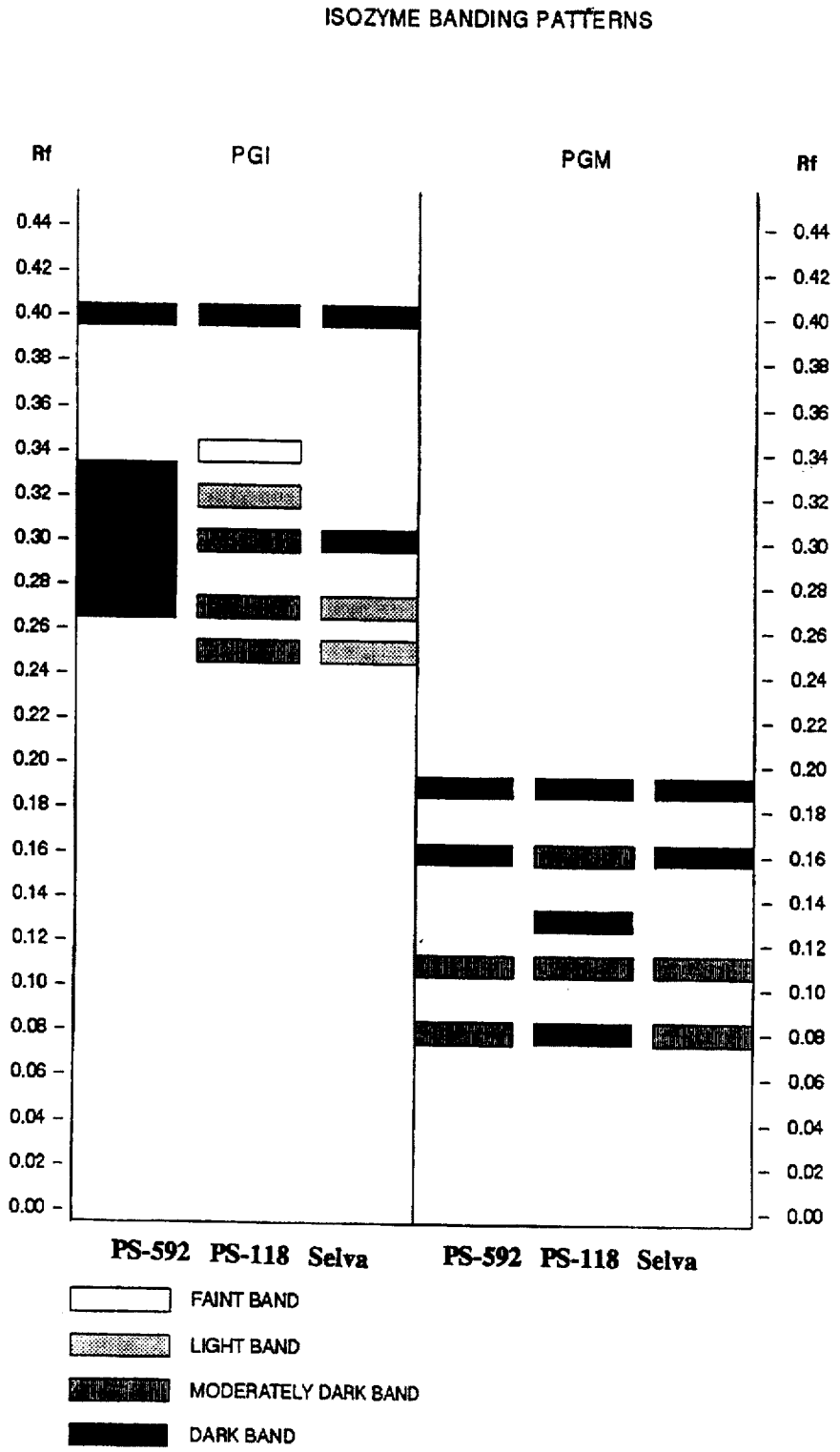
FIG. 5 discloses the isozyme banding paterns for 'PS-592' compared with those of 'PS-118' and 'Selva'.

The isozyme banding patterns of 'PS-592', compared to 'Selva' and 'PS-118', are given in FIG. 5. The pattern and band densities of PGM are distinctly different between 'PS-592' and 'PS-118'. The PGM banding pattern for 'PS-592' and 'PS-118' are designated C2 and C4 respectively. The pattern and band densities of PGI are unique and separate 'PS-592' from all other patented varieties based on a new pattern. The PGI banding pattern for 'PS-592', 'PS-118' and 'Selva' are designated A8, A7 and A2, respectively. The A8 banding pattern differs from A2 and A7 in that A8 has one continuous dark band from RF values 0.274 to 0.328. The combination of isozyme patterns shown, derived from the specific techniques described, identify 'PS-592' with certainty as a unique strawberry variety.

A series of molecular markers have been assigned to this new variety for unique identification.

PEST REACTIONS

The new variety may not be resistant to any of the known insects, diseases or viruses common in California. It is known to be moderately susceptible to the two-spotted spider mite, aphid and flower thrip. It is also known to be moderately susceptible to grey fruit mold, angular leafspot and only slightly susceptible to powdery mildew. The susceptibility of the new variety to any of the virus complexes of California has not been determined.

We claim:

1. A new and distinct variety of strawberry plant designated 'PS-592', as herein described and illustrated.

* * * * *

UNITED STATES PATENT AND TRADEMARK OFFICE

CERTIFICATE OF CORRECTION

PATENT NO. : PP09,903

DATED : May 27, 1997

INVENTOR(S) : Stephen M. ACKERMAN

It is certified that error appears in the above-identified patent and that said Letters Patent is hereby corrected as shown below:

Please note the following typographical errors:

Column 1, item [73], "Berry Red, Inc.", should read --Berry R & D--.

Signed and Sealed this

Twenty-ninth Day of May, 2001

*Attest:*

Nicholas P. Godici

NICHOLAS P. GODICI

*Attesting Officer*

*Acting Director of the United States Patent and Trademark Office*

UNITED STATES PATENT AND TRADEMARK OFFICE

CERTIFICATE OF CORRECTION

PATENT NO. : PP 09,903
APPLICATION NO. : 08/584,324
DATED : May 27, 1997
INVENTOR(S) : Stephen M. Ackerman It is certified that error appears in the above-identified patent and that said Letters Patent is hereby corrected as shown below:

Please note the following typographical errors:

Column 1, item [73], "Berry Red, Inc.", should read --Berry R & D--.

.

Signed and Sealed this

Thirty-first Day of March, 2009

John Doll

JOHN DOLL
*Acting Director of the United States Patent and Trademark Office*